United States Patent [19]

Cordonnier et al.

[11] Patent Number: 5,248,607
[45] Date of Patent: Sep. 28, 1993

[54] MONOCLONAL ANTIBODIES AND HYBRIDOMAS SPECIFIC FOR GREEN-OAT PHYTOCHROME

[75] Inventors: Marie-Michele Cordonnier, Durham, N.C.; Lee Pratt, Athens, Ga.; Sandy Stewart; Alice Montoya, both of Durham, N.C.

[73] Assignee: Ciba-Geigy Corporation, Hawthorne, N.Y.

[21] Appl. No.: 263,618

[22] Filed: Oct. 27, 1988

[51] Int. Cl.$^5$ .................. C12N 5/12; C12P 21/08; C07K 15/28
[52] U.S. Cl. ............... 435/240.27; 530/388.1; 530/391.1; 530/370; 435/172.2; 435/70.21
[58] Field of Search .............. 530/387, 370, 388.1, 530/391.1; 435/240.27, 172.2, 70.21

[56] References Cited

PUBLICATIONS

Cordonnier, et al. (1988) J. Cell Biochem Suppl O (12 Part C) p. 169, 1988.
Konomi et al. (1987) Plant Cell Physiol 28: 1443–1451.
Shimazaki et al. (1985) Planta 164: 333–344.
Pratt et al. (1987) in *Phytochrome and Photoregulation in Plants*, M. Furuya, ed., Academic Press, Tokyo, pp. 83–94.
Tokuhisa et al., Planta, 164:321–332 (1985).
Cordonnier et al., *Biochemistry*, 25:7657–7666 (1986).

*Primary Examiner*—Che S. Chereskin
*Attorney, Agent, or Firm*—Shawn P. Foley; Steven R. Lazar

[57] ABSTRACT

The present invention provides a novel method to purify green-plant phytochrome; the production of hybridoma cell lines secreting monoclonal antibodies specific for green-plant phytochrome and that do not cross-react significantly with etiolated-plant phytochrome; a partial amino acid sequence for an immunoaffinity-purified green-plant phytochrome; oligonucleotide probes for cloning green-phytochrome genes from plant genomic DNA and cDNA libraries; and cloned green-phytochrome genes and cDNA.

6 Claims, No Drawings

MONOCLONAL ANTIBODIES AND HYBRIDOMAS SPECIFIC FOR GREEN-OAT PHYTOCHROME

This research was supported in part by a grant from the United States Federal Government.

FIELD OF THE INVENTION

The present invention relates to the purification of phytochrome from green (i.e., light-grown) plants, the production of hybridoma cell lines that produce monoclonal antibodies that react selectively with green-plant phytochrome, and the identification of green-phytochrome gene and cDNA.

BACKGROUND OF THE INVENTION

Phytochrome is a photoreceptor for photomorphogenic responses in plants. That is, phytochrome detects the natural radiation of the plant environment and regulates adaptive growth and developmental responses critical for competition and survival. Phytochrome exists in two photointerconvertible forms: a red-light-absorbing form (Pr) and a far-red-light-absorbing form (Pfr). Thereby, the phytochrome system detects the ratio of red light (R) relative to far-red light (FR) and initiates appropriate morphological adaptation. For example, a low R:FR ratio could indicate the presence of shade from neighboring plants and initiate competitive morphological responses (e.g., increased shoot extension rate).

Historically, most of the understanding of phytochrome derived from the study of this chromoprotein as isolated from etiolated (i.e., dark-grown) plants, rather than from green (i.e., light-grown) plants. This is because phytochrome is relatively abundant in etiolated plants, while it is present in green plants in about 50-fold lower quantity. Further, the presence of chlorophyll in green plants makes the spectral assay of phytochrome impractical in green tissues.

Recent studies on phytochrome from green plants have indicated that it is different from phytochrome from etiolated plants. It has been hypothesized that green phytochrome and etiolated phytochrome could derive from different genes. Phytochrome of the type that is most abundant in etiolated plants is referred to herein by the term etiolated phytochrome, and, conversely, that which is most abundant in green plants is referred to herein by the term green phytochrome. However, the use of these terms is not meant to imply that there is no green phytochrome in etiolated plants, nor that there is no etiolated phytochrome in green plants. In fact, it has been observed in oat plants that etiolated plants contain a small amount of green phytochrome. (Shimazaki, Y. and L. H. Pratt, *Planta* 164 333-344, 1985).

Monoclonal antibodies directed to etiolated-oat phytochrome have been previously obtained and it has been demonstrated that most do not bind green-oat phytochrome (Tokuhisa, J. G., et al., *Planta* 164, 321-332, 1985; Shimazaki, Y. and L. H. Pratt, *Planta* 164 333-344, 1985). One monoclonal antibody directed to etiolated-pea phytochrome (Pea-25) is able to cross-react with at least some of the phytochrome from green oat shoots. The production of monoclonal antibodies specific for green phytochrome and that do not cross-react significantly with etiolated phytochrome has proven to be difficult because of the fact that green phytochrome is a very low abundance chromoprotein, estimated to be about 0.002% of extractable protein. Moreover, it is a very labile protein, and prior purification attempts yielded a relatively poor immunogen. Apparently, immunodominant contaminants were present in the prior method for green phytochrome purification and generated monoclonal antibodies directed primarily to the immunodominant contaminants.

Two hybridomas (designated GO-1 and GO-2) that were previously reported by the Applicants of the present invention (Pratt, L. H., and M.-M. Cordonnier, In *Phytochrome and Photoregulation in Plants*, Edited by M. Furuya, pp. 83-94, Academic Press, Tokyo, 1987) were prepared by immunizing with partially-purified green-phytochrome immunogen that was purified through hydroxyapatite chromatography as described by Shimazaki and Pratt (1985), and additionally purified by DEAE chromatography prior to electrophoretic purification. However, the GO-1 and GO-2 hybridoma cell lines have proven to be not sufficiently specific for green phytochrome to serve as the needed probes for resolution of phytochrome into individual species and identification of phytochrome proteins encoded by separate phytochrome genes. GO-1 by direct Elisa tested against etiolated phytochrome vs green phytochrome reacted better with etiolated phytochrome than green phytochrome. The Elisa data for GO-2 indicated that its activity was no more specific than a non-immune mouse control.

SUMMARY OF THE INVENTION

Resolution of phytochrome into individual species and isolation of the separate genes postulated to encode for the separate species of phytochrome is dependent upon the development of methods for purifying green phytochrome and the production of hybridoma cell lines which produce monoclonal antibodies that are selective for green phytochrome. In order to characterize green phytochrome fully, as well as to do so independently of etiolated phytochrome, it is important to obtain antibodies that are directed to green phytochrome, that do not cross-react significantly with etiolated phytochrome, and that react with green phytochrome sufficiently well to permit their use in sensitive quantitative assays such as ELISA, and for immunopurification.

Accordingly, the present invention addresses a number of objectives:

a) A method for purification of green phytochrome that improves purity and eliminates immunodominant contaminants;

b) Production of hybridoma cell lines secreting monoclonal antibodies that are specific for green phytochrome, that do not cross-react significantly with etiolated phytochrome, and that react well with green phytochrome that is undenatured, as well as denatured.

c) Immunoaffinity purification of green phytochrome and protein sequence analysis of immunoaffinity-purified green phytochrome to demonstrate unequivocally for the first time that green phytochrome is encoded by a separate gene (or genes) than that which encodes for etiolated phytochrome.

d) Design of oligonucleotide probes for green phytochrome genes based on the protein sequence of immunoaffinity-purified green phytochrome.

e) Cloning and purification of green phytochrome promoters and structural genes from genomic libraries for various plants; and cloning green-phytochrome cDNAs from cDNA libraries for plants.

As described fully in Example I below, green phytochrome from oats was purified by poly (ethylenimine) and ammonium sulfate fractionation, hydroxyapatite (HA) chromatography, and a second ammonium sulfate fractionation. Iodoacetamide was used throughout as a protease inhibitor. HA-purified phytochrome was further separated by SDS PAGE. Its location was identified by its $Zn^{+2}$-induced fluorescence. After staining with Coomassie blue, phytochrome bands were excised, stacked 7–8 at a time in the sample well of a second SDS gel, electrophoresed, transferred to nitrocellulose and visualized first by $Zn^{+2}$-induced fluorescence followed by staining with Ponceau S. Phytochrome-containing bands were excised, washed extensively with water, dried, dissolved in dimethylsulfoxide, emulsified with Freund's adjuvant, and injected into BALB/c mice.

As described in Example II below, hybridomas GO-4, GO-5, GO-6, GO-7, GO-8 selective for green phytochrome were produced; monoclonal antibodies were immunopurified with a column of immobilized rabbit antibodies to mouse immunoglobulins.

In Example III below, the immunoaffinity purification of green phytochrome using GO-5 monoclonal antibodies is described. Protein sequence analysis of immunoaffinity-purified green phytochrome yielded a partial amino acid sequence which when compared with the known amino acid sequence for etiolated phytochrome demonstrated for the first time that green phytochrome is encoded by a separate gene (or genes) than that which encodes for the amino acid sequence of etiolated phytochrome. From the partial amino acid sequence for green phytochrome, oligonucleotide probes were designed which may be used in standard methods known and used by those of skill in the art to clone and isolate green-phytochrome promoters and structural genes from plant genomic libraries and to clone and isolate green-phytochrome cDNAs from plant cDNA libraries. Example IV describes the procedures to be used to clone green-phytochrome genes.

The invention described herein has many important applications. Monoclonal antibodies that are specific for green phytochrome can be used to quantitate green phytochrome. Further, green plant phytochrome is important in a plant growing in a natural environment, such as an agricultural field, and influences crop yields in many plants. Thus, the isolation of green-plant phytochrome genes is essential for the eventual genetic manipulation of plants to increase plant productivity in a natural environment.

DESCRIPTION OF THE DEPOSIT

On Oct. 27, 1988, the following three hybridoma cell lines were deposited with the American Type Culture Collection, Rockville, Md., U.S.A.:

GO-5 14.9.88 JJB having the ATCC Accession No. HB9885
GO-7 15.9.88 JJB having the ATCC Accession No. HB9886
GO-8 15.9.88 JJB having the ATCC Accession No. HB9887

DETAILED DESCRIPTION OF THE INVENTION

Example I—Purification of Green Phytochrome

This purification procedure for green phytochrome is a novel procedure which allows an increase in scale, eliminates immunodominant contaminants and markedly improves both the purity and yield of green phytochrome. In particular, in contrast to previous attempts to purify green phytochrome, a reduction to 36% in the amount of $(NH_4)_2SO_4$ used for the initial fractionation markedly increased purity without significantly influencing yield. Further, a large reduction in the amount of buffer used to dissolve the $(NH_4)_2SO_4$ pellet did not alter yield, but did increase purity significantly, presumably by reducing the amount of contaminating proteins that were dissolved. The previous use of DEAE-agarose chromatography was eliminated here and two SDS gels are provided.

A) Plant material. Shoots were harvested from etiolated oats (*Avena sativa* L. cv. Garry) grown for 5 days at 25° C. in total darkness and high humidity. See Pratt, L. H., *Plant Physiol.* 51, 203–209 1973., incorporated herein by reference. Green oats were grown for a period of 10 to 11 days under natural illumination in a greenhouse. Leaves were harvested in daylight, just before sunset. Harvested tissue was immediately frozen and stored at −20° C. until used.

B) Spectrophotometric assay. Phytochrome was measured by photoreversibility assay at 664 and 728 nm for etiolated phytochrome, and at 653 and 720 or 728 nm for green phytochrome, using a fully automated, custom-built, dual-wavelength spectrophotometer similar in principle to that described by Pratt, L. H., J. E. Wampler and E. S. Rich, Jr., *Anal. Instrument.* (N.Y.) 13, 269–287 (1985). Phytochrome quantities from etiolated oats were calculated from $\Delta\Delta A$ units (Pratt, L. H. *Encycl. Plant Physiol., New Ser.* 16, 152–177, 1983) using extinction coefficients obtained by Litts, J. C., J. M. Kelly and J. C. Lagarias, *J. Biol. Chem.* 258, 11025–11031, (1983). Green phytochrome amounts were estimated similarly by assuming that it has the same extinction coefficients as does etiolated phytochrome. In both cases, one $\Delta\Delta A$ unit is about 1 mg of phytochrome. One unit (U) of phytochrome is the quantity that gives, in a volume of 1 ml and for a light path of 1 cm, a $\Delta\Delta A$ of 1.0 at the above wavelengths. Immunoprecipitates and resultant supernatants were assayed after addition of $CaCO_3$ as a scattering agent (500 mg/400 ul sample), which increases the effective optical light path (Butler, W. L. *Opt. Soc. Am.* 52, 292–299, 1962).

Absorbance spectra of hydroxyapatite-purified preparations of phytochrome were obtained with a split-beam diode-array spectrophotometer (Hewlett Packard 8452A) interfaced with a PC's Limited $286^8$ microcomputer (Dell Computer Corp., Austin, Tex.) and operated with custom-written software (Wampler, J. E., M. G. Mulkerrin and E. S. Rich, Jr., *Clin. Chem.* (*Winston-Salem, N.C.*) 25, 1628–1634, 1979; Rich, E. S. Jr. and J. E. Wampler, *Am. Lab.* (*Fairfield, Conn.*) 14, 17–28, 1982). The sample cuvette was cooled with circulating ice water.

C) Phytochrome purification. All work with phytochrome was done under green light with phytochrome maintained at or below 2° C., unless otherwise specified, or until phytochrome was denatured with SDS sample buffer.

For purification of green phytochrome, frozen green oat shoots, chopped into 3–4-cm long pieces with a sharp razor blade, were extracted in 500-g lots with 375 ml of extraction buffer in a 4-1 Waring Blender. The extraction buffer, which consisted of 0.1M tris-Cl, 0.14M $(NH_4)_2SO_4$, 10 mM EDTA and 50% ethyleneglycol, was chilled to $-20°$ C. before use. Iodoacetamide was freshly added, as a protease inhibitor, from a 0.2M stock solution to a concentration of 18 mM in the extraction buffer and 10 mM in all subsequent buffers. In addition, 0.87 g of sodium bisulfite was added immediately prior to homogenization of the tissue. As soon as the tissue was thoroughly extracted, it was filtered rapidly by centrifugation through a layer of Miracloth in a Braun MP50 juice extractor. Ten milliliter of 10% (v/v) poly(ethylenimine) was added per liter of filtrate, which was then mixed for 1 minute and centrifuged for 15 minutes at 25,000 g. $(NH_4)_2SO_4$ at 95% saturation and containing 10 mM iodoacetamide at pH 7.8 was added to the supernatant to a final concentration of 36%. After stirring for 1 minute, the preparation was centrifuged for 15 minutes at 25,000 g. The pellet was dissolved in 25 ml of resuspension buffer (50 mM tris-Cl, 5 mM EDTA, 10 mM iodoacetamide, 25% (v/v) ethylene glycol, pH 7.8 at 4° C.), clarified, frozen in liquid $N_2$, and stored at $-80°$ C. Eight such preparations were accumulated for further purification by hydroxyapatite chromatography.

The eight preparations were thawed, clarified by centrifugation for 10 minutes at 50,000 g, and diluted to a total volume of 1360 ml with resuspension buffer. The combined sample was passed through a 200-ml bed-volume hydroxyapatite column (Pratt, L. H., In *Techniques in Photomorphogenesis*, Edited by H. Smith and M. G. Holmes, pp. 175-200, Academic Press, London, New York, 1984) equilibrated with resuspension buffer containing 70 mM $(NH_4)_2SO_4$. The column was washed first with 400 ml of 50 mM tris-Cl, 5 mM EDTA, 10 mM iodoacetamide, pH 7.8 at 4° C., then with 400 ml of 5 mM K-phosphate, 5 mM EDTA, 10 mM iodoacetamide, pH 7.8. Phytochrome was eluted with a linear gradient prepared from 600 ml each of 5 mM and 200 mM K-phosphate, each containing 5 mM EDTA and 10 mM iodoacetamide at pH 7.8. The column was operated throughout at 8 ml/min. The peak fractions were kept as pool I, while the adjacent fractions on either side of the peak were kept as pool II (see Table 1 below). Phytochrome was precipitated by addition of 95% saturation $(NH_4)_2SO_4$ containing 10 mM iodoacetamide at pH 7.8 to a final concentration of 30%, collected by centrifugation for 15 min at 40,000 g, redissolved in 0.1M Na-phosphate, 1 mM EDTA, pH 7.8, frozen in liquid $N_2$, and stored at $-80°$ C.

D) Electrophoresis and electroblotting. SDS-polyacrylamide gel electrophoresis (Laemmli, U. K., *Nature* (London) 227, 680-685 1970) and electroblotting (Towbin, H., T. Staehelin and J. Gordon, *Proc. Natl. Acad. Sci. USA* 76, 4350-4354, 1979) were done as described in Pratt, L. H. et al., In *Modern Methods of Plant Analysis, New Series*, Vol. 4, Edited by H. F. Linskens and J. F. Jackson, pp. 50-74, Springer-Verlag, Berlin, 1986, incorporated herein by reference. When phytochrome was visualized in a gel by $Zn^{+2}$-induced chromophore fluorescence under UV light, $Zn^{+2}$ was included both in the gel and running buffers as described by Berkelman, T. and J. C. Lagarias, *Anal. Biochem.* 156, 194-201, (1986). When $Zn^{+2}$-induced phytochrome fluorescence was visualized on nitrocellulose, 1 mM $Zn^{+2}$ was also added to the electrotransfer buffer. Molecular weight standards were obtained from Sigma (SDS-6H).

E) Phytochrome preparation for immunization. Samples of 30 ul of hydroxyapatite-purified green-oat phytochrome (about 1 ug phytochrome) prepared in SDS sample buffer were added to each of 20 lanes of a 5-10% linear-gradient, SDS polyacrylamide gel (11 cm×14 cm) (Laemmli, U. K., *Nature* (London) 227, 680-685, 1970). After electrophoresis, the position of phytochrome in preliminary gels was visualized by its $Zn^{+2}$-induced fluorescence (Berkelman, T. and J. C. Lagarias, *Anal. Biochem.* 156, 194-201, 1986), in which case the positions of the fluorescent bands were marked by punching holes in the gel. The gel was then stained with Coomassie blue and phytochrome-containing bands were excised. The excised bands were boiled in SDS sample buffer, placed 7 at a time into each lane of a 6%, 10-lane, SDS polyacrylamide gel (ca. 6 cm×14 cm), and re-electrophoresed. This second gel was short, having a stacking gel that was about half its total length. The re-electrophoresed phytochrome was electrotransferred to nitrocellulose, on which it was again visualized by $Zn^{+2}$-induced fluorescence in initial preparations, as well as by Ponceau S stain. When $Zn^{+2}$-induced fluorescence was observed, the fluorescent bands were marked by outlining them with a pencil. The portion of the nitrocellulose bearing phytochrome was excised, washed exhaustively with water, and air dried for storage at room temperature.

F) Results. Modification of the previously used procedure for purification of phytochrome (Shimazaki, Y. and L. H. Pratt, *Planta* 164, 333-344, 1985) improved markedly both its purity and yield (Table 1). Based on extinction coefficients published by Lagarias, J. C., et al., *Photochem. Photobiol.* 46, 5-13, (1987), and on the assumption that phytochrome from both etiolated and

TABLE 1

Summary of green-oat phytochrome content, purity and yield during purification. Entries are averages of five sequential purifications, each from 4 kg of green oat leaves.

| | Volume (ml) | Phytochrome mU/ml | Phytochrome mU | Protein[1] mg/ml | Protein[1] mg | Purity[2] | Yield (%) |
|---|---|---|---|---|---|---|---|
| First $(NH_4)_2SO_4$ cut | | | | | | | |
| Before dilution[3] | 220 | 5.75 | 1265 | 5.40 | 1190 | 1.07 | 100 |
| After dilution | 1360 | 0.70 | 952 | 0.92 | 1251 | 0.76 | 75 |
| Hydroxyapatite | | | | | | | |
| Pool I | 89 | 4.53 | 403 | 1.45 | 129 | 3.1 | 32 |
| Pool II | 66 | 2.97 | 196 | 1.42 | 94 | 2.1 | 15 |
| Second $(NH_4)_2SO_4$ cut | | | | | | | |
| Pool I | 3.8 | 107 | 407 | 18.3 | 70 | 5.8 | 32 |
| Pool II | 3.1 | 56 | 174 | 19.7 | 61 | 2.8 | 14 |

[1]Protein content estimated by Bradford assay (Bradford, 1976), with reference to bovine serum albumin.
[2]Phytochrome purity is expressed as mU/ml phytochrome divided by mg/ml protein.
[3]Sum of 8 500-g preparations after resuspension and clarification, but before freezing.

green oat shoots have the same extinction coefficients, the hydroxyapatite-purified phytochrome obtained here is about 0.5% pure, which represents an estimated 250-fold purification.

Green-oat phytochrome samples prepared as described herein, were at least 10-fold more concentrated, more free of contaminating pigmentation, and significantly purer than those described previously (Tokuhisa, J. G., et al., *Planta* 164, 321– 332, 1985; Shimazaki, Y. and L. H. Pratt, *Planta* 164, 333–344, 1985; Cordonnier, M.-M., et al., *Planta* 15, 369–376, 1986). By including iodoacetamide as a protease inhibitor, phytochrome was obtained which exhibited on immunoblots predominantly, although not exclusively with all monoclonal antibodies, a single immunostained band near 124 kDa. This band co-migrates with the green-oat phytochrome that is immunostained when SDS sample buffer extracts of lyophilized, green oat leaves are immunoblotted (see Cordonnier, M.-M., et al., *Planta* 15, 369–376, 1986).

The purification procedure for green phytochrome described herein eliminated immunodominant proteins, as well as minimized degradation that previously had been found to occur. The latter was important because the contaminating proteins were about 115-kDa in size, about the same as proteolytically degraded green phytochrome. Hydroxyapatite-purified phytochrome, prepared as described here, is free of these contaminants. Moreover, by cutting out only the Coomassie blue-stained band immediately above the 116-kDa β-galactosidase marker while ignoring that just below it, monoclonal antibodies directed to green phytochrome could be obtained. With such electrophoretically purified phytochrome, monoclonal antibodies to contaminating proteins were never observed. Thus, it appears that the protein band detected on the second SDS gel, which correlates precisely with $Zn^{+2}$-induced fluorescence of the phytochrome chromophore, contains only phytochrome. This concentration step was essential to minimize the amount of nitrocellulose and dimethylsulfoxide injected with phytochrome during immunization.

Example II—Production of Hybridoma Cell Lines

Five new hybridoma cell lines GO-4, GO-5, GO-6, GO-7, GO-8 secreting monoclonal antibodies directed to green-oat phytochrome were produced by the following method.

A) Hybridomas and Antibodies. Female BALB/c mice were immunized with dimethylsulfoxide-dissolved nitrocellulose (b 50 ul/cm$^2$) that contained electrophoretically purified green-oat phytochrome and that was emulsified with an equal volume of complete Freund's adjuvant. An estimated 32–40 ug of phytochrome was injected. Mice were similarly re-injected one month after the first injection with the same amount of phytochrome, then again with the same amount 14 days later, except that incomplete Freund's adjuvant was used. Three days after the last injection, spleens were harvested and fusions performed as described in Cordonnier, M.-M., et al., *Planta* 15, 369–376, 1983, incorporated herein by reference. Fusion products were screened both by immunoblotting and by an amplified ELISA. Positive cell lines were subcloned and expanded for antibody production, as well as preserved by freezing and cryogenic storage.

Antibodies were immunopurified as described in Cordonnier et al., 1983. Oat-3, Oat-9, Oat-22 and Pea-25 have been characterized previously (e.g., Shimazaki and Pratt, 1985; Cordonnier, M.-M., H. Greppin and L. H. Pratt, *Biochemistry* 25, 7657–7666, 1986). Polyclonal rabbit antibodies to phytochrome are directed to ca. 120-kDa etiolated-oat phytochrome. Antiphytochrome immunoglobulins were purified by adsorption to and elution from a column of immobilized, ca. 120-kDa etiolated-oat phytochrome (Pratt, L. H., In *Techniques in Photomorphogenesis*, Edited by H. Smith and M. G. Holmes, pp. 175–200, Academic Press, London, New York, 1984).

B) Immunoblotting. Electroblots of SDS polyacrylamide gels were immunostained as described in detail in Pratt, L. H., et al., In *Modern Methods of Plant Analysis, New Series*, Vol. 4, Edited by H. F. Linskens and J. F. Jackson, pp. 50–74, Springer-Verlag, Berlin, 1986, incorporated herein by reference. The protocol utilizes mouse monoclonal antibody followed by rabbit antibodies to mouse immunoglobulins and alkaline phosphatase-conjugated goat antibodies to rabbit immunoglobulins, or rabbit antibodies followed by goat antibodies to rabbit immunoglobulins and alkaline phosphatase-conjugated rabbit antibodies to goat immunoglobulins. For screening of hybridomas, electroblots of 15-lane, 6% minigels (5.5 cm × 8 cm) were prepared, with 50 ng green-oat phytochrome per lane. The region of each lane expected to contain phytochrome was cut out and placed in a well of a 48-well culture plate Otherwise, the immunostaining protocol was as for a normal immunoblot.

C) ELISAs Details about the procedures used to perform ELISAs, as well as buffer compositions, may be found in Pratt, L. H., et al., In *Modern Methods of Plant Analysis, New Series*, Vol. 4, Edited by H. F. Linskens and J. F. Jackson, pp. 50–74, Springer-Verlag, Berlin, 1986. The screening ELISA was as in Cordonnier, M.-M., et al., *Planta* 15, 369–376, 1983, with the following modifications. (i) Wells were coated with 1 ug/ml of hydroxyapatite-purified green-oat phytochrome. (ii) The number of washes between each incubation with antibody was increased from three to five or more to reduce background. (iii) The alkaline phosphatase-conjugated rabbit antibodies to mouse immunoglobulins were diluted 1000-fold instead of 500-fold. (iv) A modified substrate that amplifies the alkaline phosphatase activity was used. (Johannson, A., et al., *J. Immunol. Meth.* 87, 7–11, 1986).

Color development occurred in two steps. First, 50 ul of 100 uM NADP (Sigma N-0505) in 50 mM diethanolamine, 1 mM $MgCl_2$, pH adjusted to 9.5 with HCl, was added to each well. After incubation for 30 min at room temperature, 100 ul of a second substrate solution was added to the first. The second substrate solution was prepared by mixing together (i) 4.8 ml of 25 mM Na-phosphate, pH 7.2, (ii) 1.2 ml of 2.75 mM tetrazolium salt (INT, Sigma I-8377) in 25 mM Na-phosphate, 20% (v/v) ethanol, pH 7.2, (iii) 15 ul of 5 mg/ml alcohol dehydrogenase (Sigma A-3263) in 50 mM tris-Cl, 40% (v/v) glycerol, 0.1 % $NaN_3$, 10 mg/ml bovine serum albumin, pH 8.0 at 25° C., and (iv) 150 ul of 5 mg/ml diaphorase (Sigma D-2381) in 25 mM Na-phosphate, pH 7.2. The alcohol dehydrogenase stock solution was stored at 4° C. to prevent loss of enzyme activity that occurred upon freezing and thawing; other stock solutions were stored in small aliquots at −20° C. After incubation for 30 minutes at room temperature, or until sufficient purple color had developed, the reaction was stopped by the addition of 50 ul of 0.4N HCl. The ELISA plate was assayed at 500 nm as quickly as possible, since the reaction product precipitates with time.

D) Immunoprecipitations. The general protocol used here was identical to that described in Shimazaki, Y. and L. H. Pratt, *Planta* 164, 333–344, 1985; Cordonnier, M.-M., et al., *Biochemistry* 25, 7657–7666, 1986, except for the specific ratios of antibody to phytochrome used. An immunoprecipitate of etiolated-oat phytochrome was prepared by mixing 16.5 ug of hydroxyapatite-purified etiolated-oat phytochrome with 3.3 ug of monoclonal antibody Oat-3, which is equivalent to 3 phytochrome monomers per antigen-binding site. *Staphylococcus aureus* cells (Pansorbin; Calbiochem-Behring, La Jolla, Calif. U.S.A.) were used as before to precipitate the monoclonal antibody with bound phytochrome. The amount of phytochrome in the pellet was estimated from the amount remaining in the supernatant, as assayed spectrophotometrically.

Immunoprecipitates of green-oat phytochrome were prepared for two purposes. In order to determine whether a given monoclonal antibody can immunoprecipitate phytochrome photoreversibility (see Table 2 below), and show that precipitated product is detected by Pea-25 monoclonal antibodies, 2 mU of phytochrome were incubated with the indicated amount of monoclonal antibody. After further incubation with 180 ul of a 10% suspension of *Staphylococcus aureus* cells and centrifugation, both pellets and supernatants were assayed for photoreversibility. Because CaCO$_3$ was used, the difference in light scattering between these two samples was essentially nullified. The second purpose is to characterize the precipitated green phytochrome.

TABLE 2

Immunoprecipitation of green-oat phytochrome photoreversibility.

| Mab | Amount (ug) | Phytochrome Pellet | Phytochrome Supernatant |
|---|---|---|---|
| GO-4 | 5 | 29 | 71 |
| GO-5 | 5 | 29 | 71 |
| GO-6 | 2 | 29 | 71 |
| GO-7 | 70 | 19 | 81 |
| GO-8 | 20 | 28 | 71 |
| Oat-9 | 20 | 21 | 79 |

Two milliunits of green-oat phytochrome were mixed with the indicated quantity of monoclonal antibody. After incubation with 180 ul of *Staphylococcus aureus* and centrifugation, both pellets and supernatants were assayed for photoreversibility. Results are normalized to 100% for the sum in each case. Phytochrome amounts in the pellets of non-immune mouse immunoglobulin controls (2–70 ug) ranged from 1 to 3%.

For preparation of immunoblots of immunoprecipitates, 4 mU of green-oat phytochrome was incubated with the following monoclonal antibodies in the indicated amounts: GO-4, 10 ug; GO-5, 10 ug; GO-6, 10 ug; GO-7, 50 ug; GO-8, 20 ug. After incubation for 2 h at 2° C., 180 ul of a 10% suspension of *Staphylococcus aureus* cells was added as before and the cells were collected by centrifugation (Shimazaki and Pratt, 1985). Pellets were washed two times in 0.05% Triton X-100, 10 mM tris-Cl, 0.15M NaCl, pH 8.0. The amount of phytochrome present in each pellet was estimated from photoreversibility assays of the corresponding supernatants.

To prepare immunoblots, double strength sample buffer was added to pellets to a final estimated phytochrome concentration of 4 ug/ml. Samples were incubated at 100° C. for 2 min and were loaded onto a 5–10% gradient SDS polyacrylamide gel.

E) Results. Five new hybrid cell lines designated GO-4, GO-5, GO-6, GO-7 and GO-8 were produced which secrete monoclonal antibodies specific for green phytochrome. Each monoclonal antibody detected a polypeptide of the same size as that stained by Pea-25 on immunoblot, shown earlier to cross react with green-oat phytochrome (Cordonnier et al., 1986), regardless of the extent of degradation of phytochrome. Except for Pea-2 and Oat-15, which recognize the same epitope as Pea-25 on immunoblot, both polyclonal antibodies (RAP) and monoclonal antibodies (Oat-13, Oat-22) to etiolated-oat phytochrome detected green-oat phytochrome either weakly or not at all. Conversely, these new monoclonal antibodies to green-oat phytochrome detected etiolated-oat phytochrome poorly, if at all, on immunoblot.

Each of the new monoclonal antibodies immunoprecipitated phytochrome-associated photoreversibility from hydroxyapatite-purified green-oat phytochrome preparations. As before (Shimazaki and Pratt, 1985), Oat-9 also immunoprecipitated photoreversibility from green-oat phytochrome preparations. The polypeptide immunoprecipitated by each of the monoclonal antibodies directed to green-oat phytochrome is immunostained well with Pea-25, but not Oat-22.

Monoclonal antibody Oat-3, which was shown previously not to immunoprecipitate green-oat phytochrome (Shimazaki and Pratt, 1985), was used to precipitate hydroxyapatite-purified etiolated-oat phytochrome. While Oat-22 detected this immunoprecipitated phytochrome well on an immunoblot, as expected, the new monoclonal antibodies to green-oat phytochrome did so only poorly, if at all, even at high protein loads.

Demonstration that monoclonal antibodies are directed to green-oat phytochrome

That the five new monoclonal antibodies described here are unequivocally directed to green-oat phytochrome is established by two observations. First, they each immunoprecipitated phytochrome photoreversibility, although in variable amounts (Table 2). Second, the precipitation product in each case was recognized by Pea-25, a monoclonal antibody directed to etiolated phytochrome that has previously been shown to cross-react specifically by immunoblot with green-oat phytochrome in crude extracts of green oat shoots (Cordonnier et al., 1986). Moreover, each of the new monoclonal antibodies detected the size decrease that accompanies partial proteolytic degradation of green-oat phytochrome, a size change not seen with the apparently immunodominant contaminants referred to above.

Cross reaction of monoclonal antibodies to green-oat phytochrome with etiolated-oat phytochrome Oat-22 has been shown previously to be specific to etiolated-oat, as compared to green-oat, phytochrome (Cordonnier et al., 1986). Its inability to cross-react by immunoblot with the precipitation products of monoclonal antibodies to green-oat phytochrome verified that the photoreversible phytochrome that these monoclonal antibodies immunoprecipitate is different from etiolated-oat phytochrome.

To investigate further the selectivity of these new monoclonal antibodies for green-oat phytochrome, they were tested against the immunoprecipitate obtained by incubation of Oat-3 with hydroxyapatite-purified etiolated-oat phytochrome. Oat-3 was selected because of its inability to immunoprecipitate phytochrome from green oat leaves (Shimazaki and Pratt, 1985). Moreover, the immunoprecipitate was made with an excess of phytochrome (3 phytochrome monomers per antigen binding site) such that any weak interaction between Oat-3 and green-oat phytochrome would be unlikely to result in direct immunoprecipitation of the immunochemically distinct phytochrome present in a green-oat phytochrome preparation. Under these conditions, monoclonal antibodies directed to green-oat phytochrome did not cross react visibly with the phytochrome that was immunoprecipitated when 10 ng of phytochrome were loaded per gel, even though Oat-3 detects it readily.

Example III—Partial Amino Acid Sequence of Green Phytochrome and Synthetic Oligonucleotide For Identifying Green Phytochrome Genes A) Immunoaffinity purification of green-oat phytochrome using GO-5 Monoclonal Antibodies Hydroxyapatite-purified green-oat phytochrome was purified on a immunoaffinity column of GO-5-monoclonal antibodies immobilized on affi-gel 10 beads (Biorad; Richmond, Calif.) The column constituted 1 mg of GO-5-monoclonal antibodies on 1 ml of packed affi-gel 10 beads.

The column was equilibrated with 25 mM Tris, 140 mM NaCl, pH 7.8 at 4° C. prior to loading approximately 250 ug of photoreversible phytochrome. The sample was reapplied several times until phytochrome was maximally bound as determined by spectrophotometric assay. The column was then washed with 1 ml of equilibration buffer containing 1M NaCl. A volume of 3ml of equilibration buffer was added. All wash solutions were spectrophotometrically monitored for phytochrome loss. A final rinse with 0.02M Tris, pH 8.0 was performed immediately prior to elution. Phytochrome was eluted with 1 ml of 1M formic acid. Residual liquid was expelled by forcing air through the column until dry. This sample was immediately placed on a Savant speed vac concentrator, reduced to a volume of approximately 75 ul and then ddH2O added to a final volume of 500 ul. This wash procedure was repeated 3 times. For the final wash, volume was reduced to approximately 150 ul. This final sample was then run on 10–15% Pharmacia Phastgels and stained with Coomassie R-250 to confirm purity and estimate quantity against a standard curve of beta-galactosidase (Sigma G-8511).

B) Protein Sequence Analysis of Immunoaffinity Purified Green-Oat Phytochrome

1) Peptide generation: Tris-HCl was added to 60 ug of immunoaffinity purified phytochrome sample received in water to a concentration of 100 mM. The protein was reduced using volatile tributylphosphine at a concentration of 0.05% under nitrogen for 30 minutes at room temperature. Following reduction, tributylphosphine was removed under vacuum in a Savant Speed-Vac for 15 minutes. No further modification of cysteines was attempted. Peptides were prepared by digestion with Lys-C (Boehringer-Mannheim) by adding enzyme to 2.0% for 24 hours at room temperature. Peptides were separated by reverse phase HPLC on a 1×250 mm Aquapore RP-300 column in 0.1% trifluoracetic acid using a gradient of 0 to 80% isopropanol: acetonitrile 1:1.

2) Amino acid sequence analysis: Automated Edman degradations were performed with an Applied Biosystems 470A gas-phase sequencer. Phenylthiohydantoin amino acids were identified using the on-line Applied Biosystems 120A PTH Analyzer.

3) Amino acid analysis: Amino acid composition was determined once on a sample of approximately 3 ug using the protocol of Bidlingmeyer, et. al., *J. Chromato. Biomed. Appl.* 336: 93–104 (1984). Gas phase hydrolysis with 6N HCl was carried out for 24 hours at 108° C. The phenylthiocarbamyl amino acid derivatives were analyzed by reverse phase HPLC on a Hewlett-Packard 1090 Liquid Chromatograph using an Applied Biosystems PTC-C18 column. The column was equilibrated in 3.5 mM sodium acetate, pH 5.4 and eluted with a stepwise gradient from 7% to 60% acetonitrile. The number of residues of each amino acid was calculated using a molecular weight of 124,000. Tryptophan and cysteine content was not determined.

4) Amino acid sequence: A partial amino acid sequence was obtained for green-oat phytochrome:
V-A-E-I-T-G-L-P-T-M-E-A-I-G-M-P-L-V-D.

The green-oat phytochrome peptide sequenced has homology with both etiolated-zucchini and etiolated-oat phytochrome.

| | | | |
|---|---|---|---|
| etiolated-zucchini phytochrome | 647 | IAELTGLPVDKAIGKHLLTLVE | 669 |
| Green-oat phytochrome | ? | VAEITGLPTMEAIG...MPLVD | ? |
| Etiolated-oat phytochrome | 649 | AAELTGLRVDDAIGRHILTLVE | 671 |
| | | uiiciiiccuciii... cciic | |
| | | 1  5  10    15 19 | |

The small letters indicate which residues are identical (i), evolutionarily conserved (c) or unrelated (u).

5) Oligonucleotides for identifying green-phytochrome gene sequences: From the sequence of amino acids and considerations known to those of skill in the art, the following oligonucleotide with permissible base substitutions noted underneath at the appropriate sites was designed:

```
CCA ACA ATG GAG GCA ATT  GGA ATG CC
..T..T      ..A..T..C   ..T
..C..C          ..C..A  ..G
..G..G          ..G     ..C
```

A preferred oligonucleotide with permissible base substitutions noted underneath at the appropriate sites is as follows:

```
CCA ACA ATG GAG GCA ATT GGA ATG CC
..T..T      ..A..T..C..T
..C                 ..G
                    ..C
```

Example IV—Cloning of Green-Plant Phytochrome Genes with Green-Phytochrome-specific Oligonucleotide Probes A) Synthesis and 5' End Labeling of oligonucleotides to be used as probes for screening of libraries.

For green phytochrome a mixture of 26-base oligonucleotides with the sequences

```
CCAACAATGGAGGCAATTGGAATGCC
  T T     A T C      T
  C                  G
                     C
``` and a second mixture of 26-base oligonucleotides with the sequences

```
GGCATTCCAATTGCCTCCATTGTTGG
   A   G A T     A A
   C             G
   G
``` are synthesized, using random base insertion on an Applied Biosystems Synthesizer and B-cyanoethylphosphoramidite chemistry. The oligonucleotides are purified by reverse-phase high pressure liquid chromatography (HPLC). 5 pmoles of the oligonucleotide mixture are kinased (Maniatis, T. et al., "Molecular Cloning—A Laboratory Manual," p. 125, Cold Spring Harbor Lab, Cold Spring Harbor, New York, 1982) using 200 uC of 32P-ATP (6000 Ci/mMole, 10 uCi/ul) and T4 polynucleotide kinase. After incubation at 37° C. for 30 minutes, the reaction is diluted to 100 ul, phenol/chloroform extracted and then precipitated with ethanol. The specific activity of the labeled oligonucleotide mixture is determined to be about $3 \times 10^6$ Cvcpm/pMole.

B) Production of Oat Libraries and Subclones

1) Isolation of Plant DNA

Nuclei are isolated from 4 day-old etiolated oat plants *Avena sativa* L. cv Garry by first freezing 35 grams of the tissue in liquid nitrogen and grinding to a fine powder with a mortar and pestle. The powder is added to 250 ml of grinding buffer (0.3M sucrose, 50 mM Tris, pH 8, 5 mM magnesium chloride, 5 mM sodium bisulfite, 0.5% NP40) and stirred on ice for 10 minutes. This mixture is filtered through six layers of cheesecloth, the liquid is transferred to centrifuge bottles and subjected to centrifugation at 700 x g for 10 minutes. The pellets are resuspended in grinding buffer and recentrifuged. The pellets are again resuspended in grinding buffer and this suspension is layered over a 20 ml cold sucrose cushion containing 10 mM Tris, pH 8, 1.5 mM magnesium chloride, 140 mM sodium chloride, 24% sucrose, 1% NP40. These tubes are centrifuged at 17,000 x g for 10 minutes. The pellets at this stage contained mostly nuclei and starch granules. High molecular weight DNA is isolated from the nuclei essentially according to Maniatis, T. et al., supra. Etiolated plants are used as cleaner DNA is obtained with this extraction protocol.

2) Production of genomic libraries and isolation of genomic clones of green oat phytochrome The plant DNA is partially digested with MboI and ligated into the BamHI site of the Lambda Dash cloning vector. the phage are packaged using the Stratagene cloning systems kit and a library with a primary titer of $2 \times 10^6$ is created. The library is then amplified to a titer of $1 \times 10^{10}$ phage/ml. To identify the phage containing green phytochrome, the plaques are lifted to Gene Screen plus (DuPont) and processed according to the manufacturers recommendations. The filters are prehybridized for four hours, and hybridized overnight at 42° C., in the manufacturer's hybridization solution containing 0.9M NaCl. The filters are then sequentially washed at a NaCl concentration of 0.9M and monitored by autoradiography increasing the wash temperature by 5° C. at each step until a constant hybridization pattern is obtained. Plaques are isolated that showed positive hybridization, replated and screened again with the probe mixture. This procedure is repeated until pure clones are obtained. Following purification of the phage clones DNA is isolated using the Lambdasorb procedure of the Promega Kit following the manufacturers instructions. The Bluescript subclones are excised from the Lambda Zap library following the manufacturers protocol or subclones are created as described above.

The Lambda clones are then mapped by standard mapping procedures (Maniatis, T. et al. supra) in order to identify unique clones. The fragments of the Lambda clones containing the sequences homologous to the oligonucleotide probe are then subcloned into Bluescript (Stratagene). The DNA sequence of the clones is obtained by a modification of the dideoxy sequencing protocol of Sanger et al., (1977 Proc. Natl. Acad. Sci. USA 74:5463) using a double stranded template with the Sequenase Kit.

3. Production of cDNA libraries and isolation of cDNA clones for green oat phytochrome Poly A+ RNA is isolated by standard techniques and a cDNA library is constructed in the Lambda Zap cloning vector (Stratagene), essentially as described (Gubler, U. and Hoffman, B. J., Gene 25, 263, 1983). 300,000 plaques are plated and duplicate plaque lifts are probed with the 32-P labeled oligonucleotide mixture 2 as described in section 1 above or by antibodies as described in section 4 below.

Once the green phytochrome cDNA clones are isolated, they are excised from Lambda Zap following the manufacturers protocol. They are then sequenced by double stranded dideoxy sequencing (Sanger et 1977 Proc. Natl. Acad. Sci. USA 74:5463).

4) Screening of cDNA libraries with antibodies to etiolated or green oat phytochrome Plaque lifts are immunologically screened as described by Young and Davis, (Proc. Natl. Acad. Sci. USA, Vol. 80:1194, 1983). The plaque lifts are screened using polyclonal antibodies (mAb's) raised to the synthetic peptide described above and monoclonal antibodies GO-5, GO-7, and GO-8. Clones which are identified by cross-reaction with these polyclonal and monoclonal antibodies and which do not cross-react with mAb's O-3, O-13 and O-22 are characterized as described above.

C) Isolation of green phytochrome genes from other plant species

1) DNA is isolated by the method of Murray & Thompson, 1980, Nuc. Acids Res. 8:4321, as modified by Taylor et al., 1982, BRL Focus 4:4–6, from Funk Zea maize line 2717, *Nicotiana tabaccum* cv xanthi, *Lycopersioum esculentum* cv UC82B, rice, wheat, and Arabidopsis.

2) Genomic libraries are prepared in Lambda Dash as described above and are screened with both the oligonucleotide mixture number one. Alternatively genomic libraries are screened with subclones of the oat genomic clone isolated above.

3) cDNA libraries are prepared from RNA isolated from the plants listed in Cl. The phytochrome clones are isolated as described previously by hybridization with nucleic acid probes and antibodies to green-oat phytochrome.

We claim:

1. A hybridoma cell line that produces monoclonal antibodies that react selectively with a green-oat phytochrome and do not cross-react significantly with etiolated phytochrome from oat plant.

2. A hybridoma cell line GO-5, GO-7 or GO-8 that produces monoclonal antibodies that react selectively with a green-plant phytochrome.

3. A monoclonal antibody that selectively binds to a green-oat phytochrome and does not cross-react significantly with etiolated phytochrome from oat plant.

4. A monclonal antibody produced by a hybridoma cell line identified as GO-5, GO-7 or GO-8.

5. The hybridoma cell line GO-5 that produces monoclonal antibodies that react selectively with a green-oat having the partial amino acid sequence:

V-A-E-I-T-G-L-P-T-M-E-A-I-G-M-P-L-V-D.

6. A hybridoma cell line that produces monoclonal antibodies that react selectively with a green-oat phytochrome, wherein said cell line is produced by using as an immunogen, a green-oat phytochrome purified by immunoaffinity chromatography utilizing monoclonal antibodies produced by a hybridoma of claim 1 or claim 2.

* * * * *